(12) United States Patent
Wada et al.

(10) Patent No.: US 6,372,481 B1
(45) Date of Patent: Apr. 16, 2002

(54) INSTANT DRY YEAST FOR USE IN FROZEN DOUGH-BAKING PROCESS

(75) Inventors: Yoshiki Wada, Saitama-ken; Setsu Hitokoto, Tokyo; Kazuhiro Hamada, Saitama-ken; Masayasu Ando, Tokyo; Yasuo Suzuki, Chiba-ken, all of (JP)

(73) Assignee: Oriental Yeast Co., Ltd., Tokyo (JP)

( * ) Notice: Subject to any disclaimer, the term of this patent is extended or adjusted under 35 U.S.C. 154(b) by 0 days.

(21) Appl. No.: 09/192,069

(22) Filed: Nov. 16, 1998

(30) Foreign Application Priority Data

Nov. 26, 1997 (JP) ............................................. 9-339498

(51) Int. Cl.[7] ............................. C12N 1/18; A21D 8/04
(52) U.S. Cl. ...................... 435/255.2; 435/942; 426/61; 426/62
(58) Field of Search .............................. 435/255.2, 942; 426/61, 62

(56) References Cited

U.S. PATENT DOCUMENTS

| | | | |
|---|---|---|---|
| 4,328,250 A | * 5/1982 | Clement et al. | 426/18 |
| 4,346,115 A | 8/1982 | Clement et al. | 426/25 |
| 4,547,374 A | * 10/1985 | Nakatomi et al. | 426/19 |
| 4,743,452 A | 5/1988 | Felske et al. | 426/19 |
| 4,764,472 A | 8/1988 | Pomper et al. | 435/256 |
| 5,262,182 A | 11/1993 | Kasahara et al. | 426/19 |

FOREIGN PATENT DOCUMENTS

| | | |
|---|---|---|
| EP | 0196233 | 10/1986 |
| EP | 0442575 | 8/1991 |
| EP | 0451896 | 10/1991 |
| EP | 0620974 | 10/1994 |
| JP | 739370 | 10/1995 |

* cited by examiner

*Primary Examiner*—Irene Marx
*Assistant Examiner*—Vera Afremova
(74) *Attorney, Agent, or Firm*—Browdy and Neimark P.L.L.C.

(57) ABSTRACT

The invention relates to the preparation of baker's yeast having both freezing tolerance and drying tolerance, which comprises drying pressed raw yeast suitable to baking from frozen dough, and screening it for instant dry yeast not interfering with its aptitude for frozen dough. Using the instant dry yeast, prepared is an instant-type, dry yeast composition of which the yeast activity is lowered little in the baking process from frozen dough that comprises freezing and storing dough and thawing the frozen dough. When the dry yeast is mixed with side materials in preparing dough and the dough is frozen and stored for a certain period of time and thereafter thawed, it still maintains its good baking capabilities. The dry yeast has the significant advantage of maintaining its original baking capabilities even in frozen and thawed dough. In particular, strain of *Saccharomyces cerevisiae* P-572, FERM BP-6148.

5 Claims, 2 Drawing Sheets

UPPER BAR: PRE-FERMENTED FOR 60 MINUTES, THEN FROZEN AND STORED FOR 2 WEEKS AT -20°C.

LOWER BAR: PRE-FERMENTED FOR 90 MINUTES, THEN FROZEN AND STORED FOR 2 WEEKS AT -20°C.

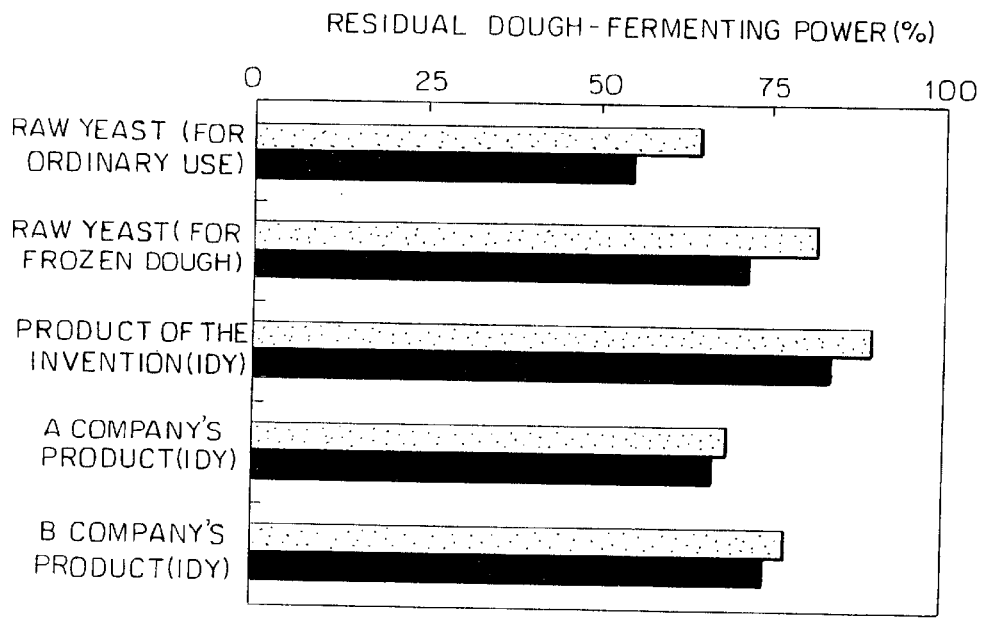
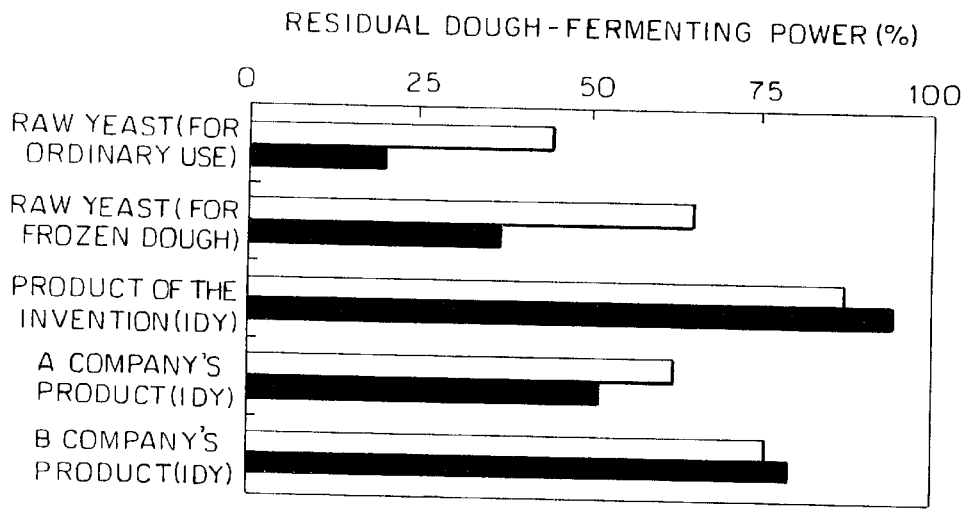

INSTANT DRY YEAST FOR USE IN FROZEN DOUGH-BAKING PROCESS

DETAILED DESCRIPTION OF THE INVENTION

1. Technical Field of the Invention

The present invention relates to baker's yeast having both freezing tolerance and drying tolerance, and more precisely, to novel dry yeast including instant dry yeast capable of being used in baking bread from frozen dough.

Though being dry, the novel yeast of the invention has excellent freezing tolerance. Frozen dough as produced through the process of preparing dough with the yeast of the invention followed by incubating and freezing it is tolerant to long-term frozen storage of 2 weeks or longer, from which is produced good bread.

Therefore, the invention greatly contributes to developments in the baking industry, especially in the frozen dough industry.

2. Prior Art

The process of baking bread from frozen dough has heretofore been developed for the purpose of saving time and labor in bakeries and for the purpose of always providing fresh bread for consumers, and is now the mainstream process in the current baking industry.

The problem with the baking process from frozen dough is that the activity of the yeast used is greatly lowered while the dough having been incubated by the action of the yeast is frozen and stored for a certain period of time, then thawed and fermented. In order to solve the problem, in general, exclusively used are freezing-tolerant yeast products in the frozen dough-baking process.

On the other hand, dry yeast as prepared by drying raw yeast has heretofore been used for the purpose of ensuring its preservability and storage stability, and is being improved. Recently, instant dry yeast (active dry yeast) products have been developed, some of which have been put into practical use.

In fact, instant dry yeast has brought about drastic improvements in baking operations over pressed raw yeast, and the storage stability of the yeast itself has been improved greatly. However, in the process of producing dry yeast, in general, if strains having drying tolerance or those having been so mutated through specific cultivation that they are tolerant to drying are not used, the activity of the yeast produced is greatly lowered after it is dried. Even if raw yeast is cultivated under specific conditions for the purpose of making it tolerant to drying to thereby obtain dry yeast, it is difficult to produce dry yeast products still having the favorable properties intrinsic to the yeast, including the fermenting ability of the yeast. The properties of dough comprising the dry yeast as prepared in that manner, and also the taste of bread from the dough will be poor. Anyhow, dry yeast could not be substituted for raw yeast in some baking conditions, because of its properties including the temperature sensitivity and the influence on the physical properties of dough.

Given that situation, at present, the application of instant dry yeast is for only specific baking processes for limited types of bread such as French bread and the like. In particular, the fermenting power of dry yeast having been kept at low temperatures, for example, in frozen dough is greatly lowered when the frozen dough that contains the yeast is thawed and fermented, like that of raw yeast products in frozen dough, and, in general, it is known that the degree of reduction in the fermenting power of dry yeast in frozen dough is greater when the pre-fermenting the dough prior to being frozen is longer and when the time for storing the frozen dough is longer. In addition, it is also known that, when contacted with water, dry yeast releases intracellular reducing substances such as glutathione and others to a much greater degree than raw yeast, thereby having some negative influences to no small extent on the physical properties of dough containing it.

In order to obviate this problem, there is an attempt to suppress the reduction in activity due to contact with low-temperature water and hydration, in which a re-hydrating agent for instant dry yeast is used in producing instant dry yeast, which is selected from specific fatty acid esters and their combinations, along with a novel activity-protecting agent that may be selected from locust bean gum, cutch gum, yeast extract, sodium carboxymethyl cellulose (CMC) and the like (see U.S. Pat. No. 4,764,472). Also employed in some cases is an antioxidant such as ascorbic acid or the like, as a stabilizer, in an amount of about 0.3% relative to the yeast product (see Japanese Patent Application Laid-Open Hei-7-39370).

However, the recent tendency in the art is toward the minimization of such additives in dough, for which freezing-tolerant instant dry yeast is desired.

SUMMARY OF THE INVENTION

Problems to be Solved by the Invention

In consideration of the current technical level in the art noted above, the present invention has been made for the purpose of newly developing novel baker's yeast having both freezing tolerance and drying tolerance.

BRIEF DESCRIPTION OF THE DRAWINGS

FIG. 2 shows the data of freezing stability of different dough samples.

FIG. 3 shows the data of influence of pre-fermentation on different dough samples.

DETAILED DESCRIPTION OF THE INVENTION

Figure 1:
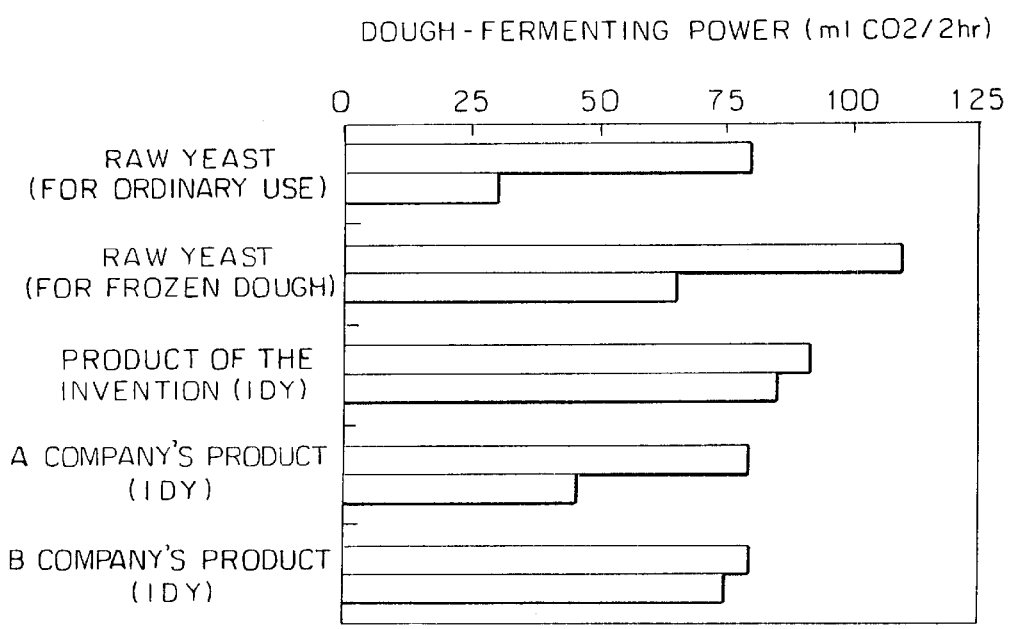
FIG. 1 shows the data of the gaseous volume of different dough samples as obtained through fermography, for which each dough sample was frozen and thawed.

In order to attain the object mentioned above, we, the present inventors have studied the related technique in all its aspects, and have specifically noted a screening method for practical baker's yeast strains. In the method, strains which have heretofore been in practical use for baker's yeast for frozen dough are screened for the intended drying-tolerant strains on the basis of the intracellular trehalose content of the strains.

However, we could not obtain the intended yeast through ordinary screening. Therefore, in order to obtain drying-tolerant yeast strains, we carried out cultivation experiments based on the intracellular trehalose content of strains.

As a result, we have succeeded in screening out one strain capable of significantly increasing the intracellular trehalose content of itself and having improved drying tolerance.

Regarding the condition for yeast culture in the experiments, employed was a feeding culture method, in which molasses was intermittently supplied to the culture system in such a manner that the time interval for the molasses supply is specifically controlled while the nitrogen source to be supplied to the system is defined on a lower level than that in ordinary yeast culture. As a result, obtained were raw yeast 1 having a nitrogen content 7.2% and a trehalose content of 13% relative to its dry weight, and raw yeast 2 having a nitrogen content of 7.4% and a trehalose content of 12% relative to the same. These raw yeasts for frozen dough, which had been cultivated for dry tolerance, were analyzed to give the data in Table 1 below.

The nitrogen content of each yeast was measured according to a Kjeldahl method; and the trehalose content and the carbohydrate content of each yeast were measured according to a phenol-sulfate method. The gassing power on liquid substrate (F(10)) was measured through fermentation recorder at 30° C., on the basis of the index by the Yeast Industry Association of Japan.

TABLE 1

|  | Cultivation for Drying Tolerance | | Ordinary Cultivation |
| --- | --- | --- | --- |
|  | Raw Yeast 1 | Raw Yeast 2 | Control |
| Trehalose (%) | 13 | 12 | 7 to 11 |
| CH (total) (%) | 37 | 36 | 30 |
| N (total) (%) | 7.2 | 7.4 | 8.2 |
| F(10) (ml $CO_2$) | 130 | 158 | 182 |

(CH: carbohydrate content, N: nitrogen content, F: gassing power)

Trehalose and CH values: measured in a phenol-sulfate method (these are relative to the dry matter weight).
N value: measured in a Kjeldahl method (this is relative to the dry matter weight).
F(10): measured through fermentation recoder (30° C.) (this is based on the index by the Yeast Industry Association of Japan).

Next, the thus-obtained raw yeasts 1 and 2 were dehydrated under pressure into compressed raw yeasts having a water content of 68%. The compressed raw yeast weighed 1.5 kg each. These were separately mixed with an aqueous emulsion of a sorbitan fatty acid ester of being from 1.5 to 2.0% by weight relative to the dry yeast, and passed through a 0.4-mm$\phi$ screen mesh in an extruder into strands, which were then dried at a constant drying rate in a fluidized bed drier for about 10 minutes. Hot air was introduced into the drier to keep the initial inlet temperature of 50° C. After this but just before the temperature of the yeast in the drier began to rise, the center part of the fluidized bed was suitably controlled to be at 38° C., and the yeast was further dried in a batch system at a decreasing drying rate for about 50 minutes. In this step, the temperature of the yeast being dried was kept to be not higher than 38° C. The end point of the drying was monitored with an infrared moisture meter, and the drying was stopped when the water content of the yeast reached 5% or lower. The thus-dried yeast was packaged in vacuum and stored.

As is obvious from the description to follow hereinunder, it was confirmed that the instant dry yeast thus prepared from yeast for frozen dough in the manner mentioned above is characterized by its ordinary use in frozen dough and by its significant advantage of increased activity (fermenting power) remaining in incubated, frozen, stored and thawed dough. Of those, the instant dry yeast derived from raw yeast 1 was deposited on Oct. 20, 1997 in the international depository authority, the National Institute of Bioscience and Human-Technology, Agency of Industrial Science and Technology of Japan, for FERM BP-6148, pursuant to the Budapest Treaty.

Using the thus-prepared instant dry yeasts 1 and 2, and also an ordinary instant dry yeast which had been prepared by cultivating the yeast strain as screened out previously and processing it in the same manner as above, produced were dough samples for loaves. Each dough sample was divided into plural portions weighing 40 g each, and fermented in an ordinary/manner, whereupon the amount of gas production per 2 hours was measured. The data thus measured are referred to as the dough-fermenting power of each yeast tested. The data are shown in Table 2.

TABLE 2

|  | Dry Yeast 1 (of the invention) | Dry Yeast 2 (of the Invention) | Ordinary Dry Yeast |
| --- | --- | --- | --- |
| Dough-Fermenting Power (ml $CO_2$/2 hr/40 g) | 74 | 60 | 30 to 55 |

Dough Formulation: for loaves, containing the instant dry yeast in an amount of 0.7% by weight relative to the amount of flour.

As mentioned hereinabove, baker's yeast having both freezing tolerance and drying tolerance could be obtained from drying-tolerant strains as screened out from yeast strains for frozen dough. However, in order to obtain dry yeast which can be used in baking from frozen dough and of which the dough-fermenting power is comparable to or higher than that of commercially-available dry yeast, the yeast strains must be further cultivated for drying tolerance.

For example, the strains are cultivated in at least any one condition for molasses feeding culture, trehalose inducible producing culture, limited feeding culture in latter stage and limited nitrogen source culture, to thereby obtain various types of the intended dry yeast having both freezing tolerance and drying tolerance. For this, the drying condition shall satisfy at least one of fluidized bed drying, use of emulsifier (from 1 to 2% by weight, for example, 1.5% by weight relative to the dry yeast), and water content control (from 2 to 7%, for example, from 4 to 5%). The emulsifier is not specifically defined, so far as it has an HLB value of from 3 to 15, preferably from 5 to 10.

The dry yeast of the invention is produced from yeast having been cultivated to satisfy its trehalose content of not smaller than 13%, preferably from 14 to 15%. If its trehalose content is smaller than 13%, the yeast could not have the intended freezing tolerance and drying tolerance.

The dry yeast of the invention is also produced from yeast having been cultivated to satisfy its nitrogen content of not larger than 7.5%, preferably from 7.0 to 7.2%. If its nitrogen content is larger than 7.5%, the yeast will have poor freezing tolerance though its fermenting power is high. On the other hand, if the nitrogen content of the yeast is smaller than 7.0%, the fermenting power thereof is too low and the yeast could not have satisfactory drying tolerance in practical use.

The budding rate of the yeast must be smaller than 6%, preferably smaller than 2%. If its budding rate is not smaller than 6%, the yeast could not be sufficiently matured and could not produce a satisfactory amount of trehalose therein. If so, the drying tolerance of the yeast is lowered, and the remaining activity thereof is also lowered.

Examples of the invention are mentioned below.

EXAMPLE 1

100 g of wheat flour was mixed with 5 g of sugar, 2 g of salt, 1.4 g of instant dry yeast (FERM BP-6148) and 65 ml of water at a mixing temperature of 28° C. to prepare dough. The dough was divided into plural portions weighing 40 g each, incubated at 30° C. for 30 to 90 minutes, and then frozen and stored at −20° C. for 1 to 2 weeks. These dough portions were thawed at 28 to 30° C. for 1 hour, and their $CO_2$ gas production per 2 hours was measured. The data thus measured indicate the dough-fermenting power of the dough.

The $CO_2$ gas production was measured through fermography at 30° C., on the basis of the index by the Yeast Industry Association of Japan.

For comparison and control, a sample of pressed raw yeast for which the strain for the dry yeast was cultivated in ordinary culture (hereinafter referred to as frozen (raw)), a sample of ordinary pressed raw yeast with no freezing tolerance (hereinafter referred to as ordinary (raw)), and two samples of commercially-available, ordinary instant dry baker's yeast (hereinafter referred to as A Company's product (IDY) and B Company's product (IDY)) were tested for their dough-fermenting power in the same baking process as above, in which any of those yeast samples was added to dough in the same amount, relative to the dry weight, as in the dry yeast-containing dough.

The test data obtained are shown in the following Tables 3 and 4 and FIG. 1.

TABLE 3

Aptitude of Compressed Raw Yeast for Frozen Dough
(in terms of gas production)

| Pre-fermen-tation | Ordinary Baker's Yeast (with no freezing tolerance) | | Baker's Yeast of the Invention for Frozen Dough (with freezing tolerance) | |
|---|---|---|---|---|
| (at 30° C.) | 1 week | 2 weeks | 1 week | 2 weeks |
| 30 (min) | 129 | 137 | 146 | 149 |
| 60 | 89 | 76 | 119 | 104 |
| 90 | 61 | 28 | 91 | 58 |

Data: dough-fermenting power (total ml $CO_2$/2 hr/40 g dough) Dough Formulation: for loaves, containing the raw yeast in an amount of 4% by weight relative to the amount of flour.

TABLE 4

Aptitude of Instant Dry Yeast for Frozen Dough
(in terms of gas production)

| Pre-fermen-tation | Instant Dry Yeast of the Invention | | Commercially-Available Instant Dry Yeast A | | Commercially-Available Instant Dry Yeast B | |
|---|---|---|---|---|---|---|
| (at 30° C.) | 1 week | 2 weeks | 1 week | 2 weeks | 1 week | 2 weeks |
| 30 (min) | 104 | 91 | 98 | 91 | 91 | 90 |
| 60 | 97 | 90 | 85 | 84 | 89 | 84 |
| 90 | 93 | 87 | 63 | 47 | 71 | 75 |

Data: dough-fermenting power (total ml $CO_2$/2 hr/40 g dough) Dough Formulation: for loaves, containing the instant dry yeast in an amount of 1.4% by weight relative to the amount of flour.

On the basis of the absolute value of the dough-fermenting power of each yeast shown in Tables 3 and 4, obtained was the ratio of the dough-fermenting power thereof in frozen and thawed dough to that in non-frozen dough, which indicates the freezing stability of each yeast. In addition, the ratio of the dough-fermenting power of each yeast in frozen and thawed dough for which the pre-fermentation was prolonged to that of the same dough for which the pre-fermentation was short was obtained, and this indicates the freezing tolerance of each yeast. These are in FIG. 2 and FIG. 3. In FIG. 2, shown is the freezing stability of each yeast for which the pre-fermentation was 60 minutes; and in FIG. 3, shown is the freezing tolerance of each yeast for which the pre-fermentation was prolonged from 30 minutes to 90 minutes.

The evaluation for the aptitude of yeast in frozen dough according to the method employed herein well reflects the aptitude of known, compressed raw yeast in frozen dough. The stability of the instant dry yeast for frozen dough of the invention that had been produced herein was entirely better than that of the other companies' instant dry yeast products.

ADVANTAGES OF THE INVENTION

According to the present invention, various novel dry yeasts including instant dry yeast with freezing tolerance were obtained for the first time. Thus, the invention has realized for the first time instant dry yeast that could not be obtained in the prior art, and has realized baking from frozen dough that contains the instant dry yeast. The invention has further promoted the industrial production of bread.

What is claimed is:

1. A biologically pure culture of *Saccharomyces cerevisiae* P-572, FERM BP-6148.

2. A ready to use dry yeast product for making bread using frozen dough which comprises dry yeast, 1 to 2% emulsifier relative to the dry yeast, 2 to 7% water, which is produced by a procedure which comprises:

(1) mixing *Saccharomyces cerevisiae* P-572, FERM BP-6148 with an aqueous emulsion of an emulsifier;

(2) supplying the mixture obtained in step (1) to an extruder; and (3) supplying the extruded mixture obtained in step (2) to a fluidized bed drier for drying the extruded mixture.

3. The ready to use dry yeast product according to claim 2 wherein the *Saccharomyces cerevisiae* is compressed for dehydration.

4. The ready to use dry yeast product according to claim 2 wherein the *Saccharomyces cerevisiae* is cultured and compressed for dehydration.

5. The ready to use dry yeast product according to claim 2 wherein the *Saccharomyces cerevisiae* is cultured, recovered, and compressed for dehydration.

* * * * *